United States Patent [19]

Halpern

[11] Patent Number: 5,001,825
[45] Date of Patent: Mar. 26, 1991

[54] CATHETER GUIDEWIRE FABRICATION METHOD

[75] Inventor: David S. Halpern, Milpitas, Calif.

[73] Assignee: Cordis Corporation, Miami Lakes, Fla.

[21] Appl. No.: 266,772

[22] Filed: Nov. 3, 1988

[51] Int. Cl.⁵ .............................................. B21D 39/00
[52] U.S. Cl. ........................................ 29/456; 72/286;
604/282; 128/772
[58] Field of Search ................. 29/456, 436, DIG. 11;
128/772; 604/282; 72/284, 343, 377, 276, 286

[56] References Cited
U.S. PATENT DOCUMENTS

| | | | |
|---|---|---|---|
| 2,095,563 | 10/1937 | Cowdery | 72/276 |
| 2,199,602 | 5/1940 | Wright | 72/284 X |
| 2,379,801 | 7/1945 | Henry | 72/343 X |
| 4,080,706 | 3/1978 | Heilman et al. | 128/772 X |
| 4,619,274 | 10/1986 | Morrison | 128/772 |
| 4,721,117 | 1/1988 | Mar et al. | 128/772 |
| 4,811,743 | 3/1989 | Stevens | 128/772 |
| 4,832,047 | 5/1989 | Sepetka et al. | 128/772 |

Primary Examiner—Joseph M. Gorski
Assistant Examiner—S. Thomas Hughes
Attorney, Agent, or Firm—Watts, Hoffmann, Fisher & Heinke Co.

[57] ABSTRACT

A fabrication process for a guidewire. A guidewire core is provided by drawing down a metal wire in stages. The wire is drawn through a first die to produce a first diameter wire. This first diameter wire is then partially drawn through a second die to provide a second, reduced diameter wire segment at one end of the core wire.

3 Claims, 1 Drawing Sheet

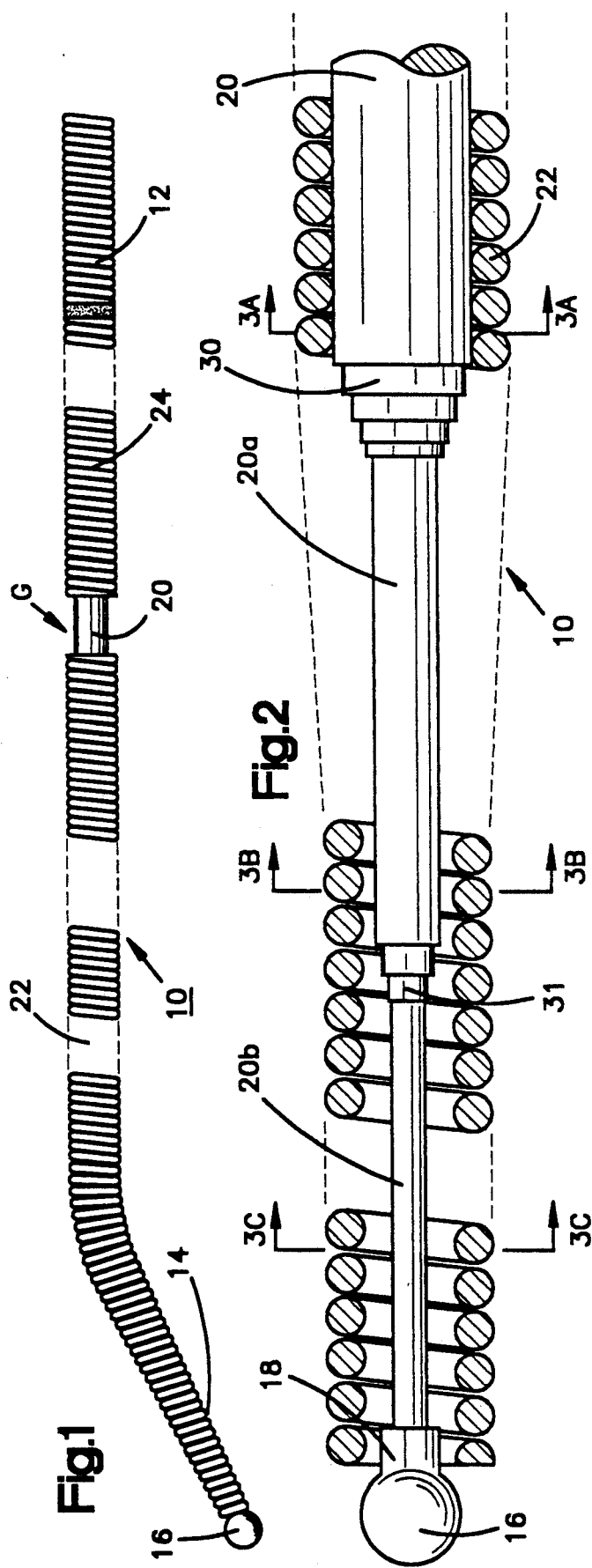

CATHETER GUIDEWIRE FABRICATION METHOD

TECHNICAL FIELD

The present invention relates to a method for fabricating a small diameter guidewire used in positioning an elongated catheter within a patient.

BACKGROUND ART

The use of elongated flexible guidewires for help in positioning both diagnostic and therapeutic catheters within a patient is well known in the prior art. In accordance with such a procedure, an elongated guidewire having a flexible tip at one end is inserted within the patient's cardiovascular system and routed into the patient. Progress of such a guidewire is monitored by an attending physician on a viewing screen. To facilitate viewing of the distal end of the guidewire as it progresses through the patient, it is known in the prior art to utilize an x-ray opaque material for the guidewire tip. Once the guidewire has been positioned within the patient, the elongated catheter is slipped over the guidewire and routed to a desired position within the patient.

Two examples of prior art guidewires are disclosed in U.S. Pat. Nos. 3,906,938 to Fleischhacker and 4,545,390 to Leary. Each of these prior art patents discloses a guidewire having a flexible spring at the guidewire's distal end. Beneath the spring is a core wire tapered to a reduced diameter. The combination of the tapered core wire and the flexible spring provides a distal tip which can be bent into a desired configuration by the attending physician prior to guidewire insertion and in addition, provides a flexible enough tip so that when interior blood vessel walls are encountered as the guidewire is inserted, the tip will bend without puncturing the blood vessel walls.

In fabricating a multi-piece guidewire, core wire is fabricated and the flexible spring then attached to the distal end of the core wire using a welding or soldering technique known in the art. Prior art fabrication techniques for the core wire involve centerless grinding of the core wire to produce a tapered transition region and reduced diameter distal end. In addition, the prior art suggests flattening the tapered end portion to increase even further flexibility of the core wire.

The prior art practice of centerless grinding the core wire to reduced diameter portion has certain limitations. During fabrication of the core wire, a drawing process is used to achieve an initial core wire diameter. During this drawing process, the outside surface of the core is work hardened. During the grinding process that tapers the core wire, the outside skin of the wire is removed and the tapered portion is softer than the larger diameter portion of the guidewire.

The prior art centerless grinding technique is difficult to perform over long lengths of small diameter wire. This is due to the fact that the small diameter wire tends to break during the grinding process. In addition, known technology cannot produce diameters small enough for certain uses wherein the guidewire must be inserted into small blood vessels.

DISCLOSURE OF THE INVENTION

The above disadvantages accompanying prior art core wire fabrication techniques are overcome by practice of the present invention. In accordance with a preferred core wire fabrication technique, the core wire is drawn in stages to produce a step-down core wire distal portion having a desired degree of flexibility.

In accordance with a method of the invention, the core wire is fabricated by first drawing a wire through a die to a first diameter of specified dimension. An end portion of the wire is drawn down to a second, smaller dimension by forcing a portion of the wire through a series of dies.

The process of drawing the wire at an end portion until a specified thickness is achieved is preferably performed in multiple stages or steps. The process of drawing the wire to narrower thickness work hardens the wire and avoids the softening of the core wire resulting from prior art grinding techniques.

Long lengths of small diameter end portions are achievable utilizing the drawing technique of the invention. It is also possible to achieve very small diameter end portions to the core wire. Stepped-down diameters as small as 0.0005 of an inch are possible.

Once the center core is constructed using the fabrication techniques of the invention, flexible spring and distal tip elements are formed using welding or soldering techniques known in the prior art. If further flexibility is needed, the reduced diameter segment of the wire can be flattened or coined.

From the above it is appreciated that one object of the invention is an improved multiple step drawing process for a core wire utilized in fabricating a catheter guidewire. This and other objects, advantages and features of the invention will become better understood from a detailed description of the fabrication process which is described in conjunction with the accompanying drawings.

BRIEF DESCRIPTION OF THE DRAWINGS

FIG. 1 is a side elevation view of a guidewire used in positioning a catheter;

FIG. 2 is a partially sectioned view of a distal end of the FIG. 1 guidewire;

FIGS. 3A, 3B and 3C are section views of a core wire as seen from the planes 3A—3A, 3B—3B and 3C—3C of FIG. 2; and FIG. 4 schematically illustrates the step of drawing a catheter core wire through a die.

BEST MODE FOR CARRYING OUT THE INVENTION

Turning now to the drawings, FIG. 1 depicts an elongated guidewire 10 suitable for guiding the insertion of a diagnostic or therapeutic catheter into a patient. The guidewire 10 has a proximal end 12 and a length sufficient to place a distal end 14 at a region of interest within the patient. An extreme distal tip 16 is sphere-like and formed by TIG welding a metal sleeve 18 (FIG. 2) that is slipped over a distal end of a guidewire core 20.

The core 20 comprises an elongated flexible stainless steel wire surrounded along most of its length by a coiled stainless steel spring 22. At a proximal end of the guidewire 10, a second flexible spring portion 24 surrounds a proximal end portion of the guidewire 10 and is attached to the core 20 by a solder connection or the like. Since the inner diameter of the flexible elongated spring is less than the TIG welded sphere at the distal tip of the guidewire 10, the elongated spring portion is trapped between the distal tip 16 and the proximal portion 24. A small gap G separates the proximal and distal spring portions 22, 24.

The guidewire length is such that the entire proximal portion 24 is outside the patient during manipulation of the distal tip within the patient and therefore the proximal spring is used by the physician to grasp the core 20 and rotate it beneath the elongated spring portion 22. Rotation of the core 20 and sphere 16 with respect to the elongated spring 22 reorients the distal end 14 of the guidewire 10. This allows the distal tip 16 to be routed into and through branching vessels along its path of entry into the patient, Further details regarding the construction of the guidewire shown in FIG. 1 may be obtained by referring to U.S. Pat. No. 4,811,743 to Steven issued March 14, 1989, which is assigned to the assignee of the present invention. The disclosure of this patent is incorporated herein by reference.

Experience with the guidewire such as that depicted in FIG. 1 indicate the center core 20 must exhibit sufficient torsional rigidity to transmit torques from the proximal end portion 24 of the guidewire 10 along the length of the guidewire to the distal end 16. In addition, it is desirable that the extreme distal portion of the guidewire be flexible enough to encounter walls of the cardiovascular system and bend or flex without puncturing the blood vessel wall. To achieve the combination of torsional rigidity and flexible distal end, the core 20, as best seen in FIG. 2, is stepped down at regions 30, 31.

The proximal portion of the core 20 has a first diameter D and an intermediate distal portion 20a of the e 20 has a reduced diameter D' to provide a greater degree of flexibility to the guidewire. In the embodiment depicted in FIG. 2, an extreme end portion 20b of the core 20 is stepped down even further at a region 31 to a third diameter D". Representative dimensions D, D', D" are 0.014, 0.005 inches, and 0.003 inches respectively.

The guidewire is fabricated by drawing the core 20 through multiple dies. The proximal spring portion 24 is then soldered to the larger diameter portion of the core wire (having a diameter D) and the elongated flexible spring portion 22 is slipped over the remaining portion of the core 20. The metal sleeve 18 is then TIG welded to the core to form the sphere-like distal tip 16.

A drawing bench includes a motorized gripper and commercially available diamond dies for processing the wires. Only one die will be used at a time and the number of dies will vary based on the diameter of the finished products. The step of drawing the wire through a representative one of such dies is illustrated schematically in FIG. 4. It is possible that up to 15 dies in increments as small as 0.001" may be used.

This process begins with wire having the major diameter D (FIG. 3A) of the desired guidewire and wire that has already been straightened and cut to length. A point is put on one end of the wire either by grinding it or heating the tip and pulling the wire to form a point. The point will act as a lead and allow the wire to go through the die. After the wire has been drawn a first amount, is removed and a next die can be pulled over the wire. This method is repeated for the appropriate number of steps until the desired diameter D'(FIG. 3B) is achieved. The distance of the drawn portion can be controlled by inserting a block of material to be used as a spacer and an end stop for the die to be pulled against.

The transition region 30 of stepped down diameters results. A separate step is formed for each die the wire is drawn through. A second transition zone or region 31 is formed in an analogous fashion by drawing the wire through even smaller diameter dies.

The wire will end up with a straight section having a diameter D and a step-down drawn length will be curved from the drawing process and not straight as it was initially. The wire is baked in an over under tension which will enable the section to straighten out. The drawn portion can then be cut to a final length. In one application, the core wire is cut into lengths of between 180 and 200 centimeters.

The stepped transition of core wire diameter is substantially different from the centerless ground core wire which has gradual or tapered transition regions between different thickness core wire portions. As noted above, one advantage of the present invention is the ability to produce a long section of reduced diameter core wire without breaking the core wire. A second improved feature is the use of multiple dies to produce as many steps in the core wire as are deemed desirable. Although a split-sleeve die is a preferred technique for producing the stepped core wire of the invention, it is appreciated that other drawing techniques for producing a stepped core wire are also envisioned. It is therefore the intent that the invention include all modifications and alterations from the disclosed fabrication technique falling within the spirit or scope of the appended claims.

I claim:

1. A method of fabricating a guidewire to be inserted within a subject comprising the steps of:
    a) providing an elongated core wire of a specified diameter and length;
    b) drawing the core wire at ambient temperature through a plurality of dies having different inner diameters thereby forming:
        a first cylindrical portion;
        a second cylindrical portion having a diameter less than a diameter of the first cylindrical portion and located distalward of the first cylindrical portion;
        a first region separating said first and second cylindrical portions, said region comprising a plurality of shouldered cylindrical steps and having less axial length than either said first or second cylindrical portion;
        a third cylindrical portion having a diameter less than the diameter of the second cylindrical portion and located distalward of the second cylindrical portions; and
        a second region separating said second and third cylindrical portions, said region comprising a plurality of shouldered cylindrical steps and having less axial length than either said second or third cylindrical portions; and
    c) surrounding at least a portion of the core wire with a flexible coiled spring.

2. A method according to claim 1 including the additional step of heating the core wire under tension after drawing thereby straightening the core wire.

3. A method according to claim 1 wherein the drawing step comprises drawing said third cylindrical section to an outer diameter less than 0.005".

* * * * *